US00PP37730P2

(12) United States Plant Patent
Schoenmakers

(10) Patent No.: US PP37,730 P2
(45) Date of Patent: Oct. 6, 2026

(54) ***FITTONIA* PLANT NAMED 'KEJAPA121'**

(50) Latin Name: *Fittonia albivenis*
Varietal Denomination: KEJAPA121

(71) Applicant: Schoenmakers Tussenholding B.V., Haaren (NL)

(72) Inventor: Jan Cornelis Adrianus Maria Schoenmakers, Haaren (NL)

(73) Assignee: Schoenmakers Tussenholding B.V., Haaren (NL)

( * ) Notice: Subject to any disclaimer, the term of this patent is extended or adjusted under 35 U.S.C. 154(b) by 0 days.

(21) Appl. No.: 19/375,362

(22) Filed: Oct. 31, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ..... A01H 5/12; A01H 5/00; A01H 6/00
See application file for complete search history.

(56) References Cited

U.S. PATENT DOCUMENTS

PP18,169 P2 * 10/2007 Schoenmakers ..... A01H 5/12
Plt./373

* cited by examiner

*Primary Examiner* — June Hwu
(74) *Attorney, Agent, or Firm* — Samuel R. McCoy, Jr.

(57) ABSTRACT

'KEJAPA121' is a new and distinctive *Fittonia* plant which is characterized by a compact growth habit, elliptic foliage with lightly undulating, crenulate margins, and an adaxial foliar surface that is colored with a bright pink-on-green tessellate variegation pattern. 'KEJAPA121' shows the stability of all these characteristics from generation to generation.

2 Drawing Sheets

Latin name of the genus and species: The Latin name of the genus and species of the novel variety disclosed herein is *Fittonia albivenis*.

Variety denomination: The inventive variety of *Fittonia* disclosed herein has been given the denomination 'KEJAPA121'.

BACKGROUND OF THE INVENTION

Parentage: 'KEJAPA121' originated as a naturally occurring, partial-plant mutation of *Fittonia albivenis* 'Mistral' (Community Plant Variety Rights Application No 2006/1501), which was discovered at a commercial greenhouse in Haaren, The Netherlands, in May of 2021. The mutation was noted for its bright pink-on-green tesselate variegation, relative to 'Mistral' which exhibits light pink-on-dark green variegation. The mutation was harvested from the parent plant and subsequently propagated by rooting stem cuttings. The resulting plants were then grown to a mature size in order to evaluate and confirm the uniformity and stability of the unique characteristics first observed. Upon confirmation, in May 2022, the inventor selected the claimed *Fittonia* plant 'KEJAPA121' for commercialization due to its unique foliage coloration that differs significantly from the parent plant.

Asexual Reproduction: Asexual reproduction of 'KEJAPA121' by way of apical meristematic division, was first performed in May of 2021 at a commercial greenhouse in Haaren, The Netherlands. Through eight subsequent generations, the plants so produced have shown that the unique features of the instant cultivar are stable and reproduced true to type.

SUMMARY OF THE INVENTION

The cultivar 'KEJAPA121' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Fittonia* cultivar 'KEJAPA121'. These traits, in combination, distinguish 'KEJAPA121' as a new and distinct cultivar.

1. *Fittonia* 'KEJAPA121' exhibits a compact growth habit, with decumbent lateral branches that become stoloniferous as the plant matures; and
2. *Fittonia* 'KEJAPA121' exhibits elliptic laminas with cross-venulate foliar venation and lightly undulating, crenulate margins; and
3. *Fittonia* 'KEJAPA121' exhibits a green adaxial foliar surface, with pink veins, and a somewhat lighter pink coloration bordering the network of veins which creates a bright pink-on-green tessellate variegation pattern.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
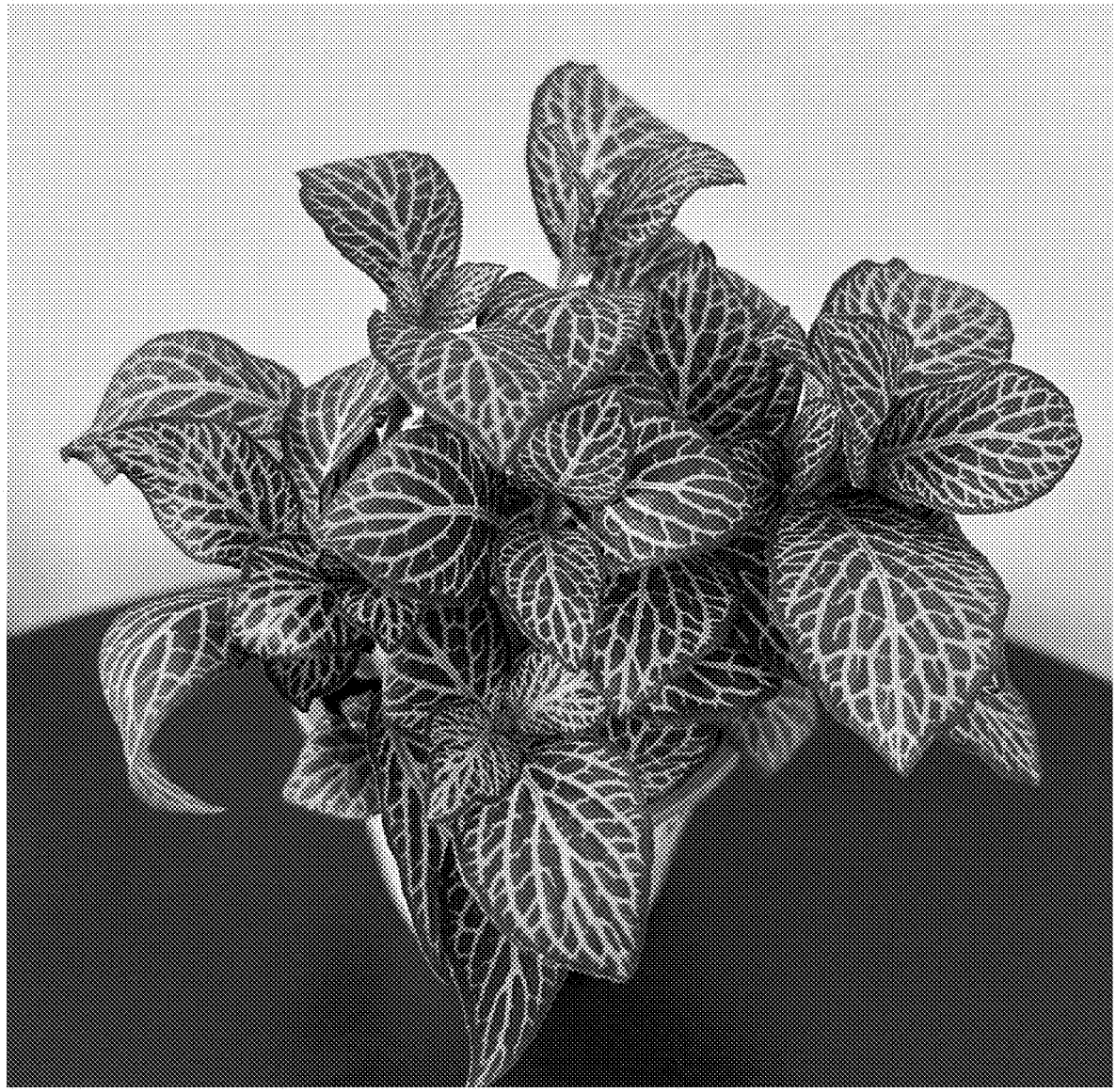
FIG. 1 shows, as nearly true as it is reasonably possible to make the same in color illustrations of this type, an exemplary plant of the new cultivar, 'KEJAPA121', approximately 15-week-old in a 350 mL nursery container. The plant shown was grown from a rooted cutting, potted into a nursery container, grown in a greenhouse in Stuarts Draft, Virginia.
Figure 2:
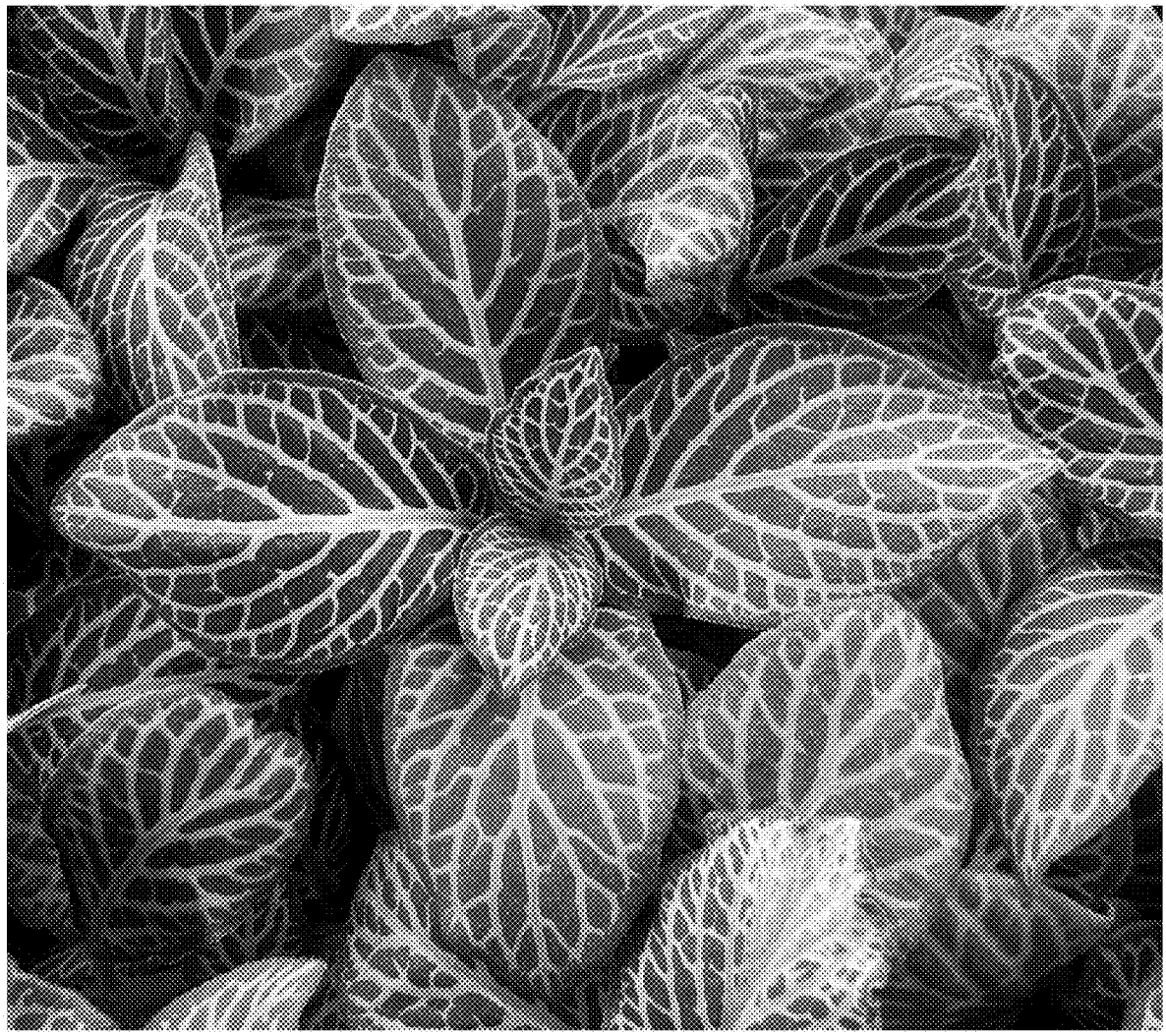
FIG. 2 illustrates the adaxial surface of the juvenile and mature foliage of the aforementioned 'KEJAPA121' plant.

The following observations and measurements were made in September of 2025. With the exception of the 51-week-old plants used to describe the stoloniferous habit of the plant, the *Fittonia* 'KEJAPA121' plants analyzed and described in this botanical description are approximately 13-week-old grown in a 350 mL nursery container. Plants were produced using conventional greenhouse production protocols for *Fittonia* species which consisted of overhead irrigation once a week, grown under shade with light levels ranging from approximately 2,000 to 4,000 lumens, with ambient temperatures ranging from 20 to 35 degrees Celsius and humidity levels ranging from 60 to 95 percent. No pest or disease measures were employed. The 51-week-old plants were grown in the same manner as the aforementioned 13-week-old plants, only they were moved to an outdoor area with rain exclusion and 30 percent shade at 30-weeks-old. These plants were manually watered as needed, and no pest or disease control measures were employed.

Those skilled in the art will appreciate that certain characteristics will vary with older or, conversely, with younger plants. 'KEJAPA121' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on *The Royal Horticultural Society Colour Chart*, The Royal Horticultural Society, London, second edition.

A botanical description of 'KEJAPA121' and comparisons with the parent plant and the most similar variety of common knowledge are provided below.

Plant description:

*Growth habit*.—Broad spreading.

*Plant form*.—Stoloniferous.

*Average height*.—10.2 cm.

*Plant spread at* 13 *weeks*.—19.2 cm.

*Propagation*.—Type — Asexual propagation is accomplished by way of rooting stem cuttings. Time to produce a rooted cutting — Approximately 4 weeks to produce a rooted cutting. Time to produce a rooted mature plant — Approximately 14-20 weeks grown in a 350 mL nursery container.

*Disease resistance*.—'KEJAPA121' exhibits susceptibility in common with the parent including bacterial leaf spot caused by *Xanthomonas campestris*, fungal blight caused by *Rhizoctonia solani*, as well as common arthropod pests such as aphids, moths, fungus gnats, and thrips.

*Environmental tolerances*.—Adapt to temperatures as high as 31 degrees Celsius. Thrives in partial shade with 60-70% humidity. Leaf scorch will occur in direct sunlight. 'KEJAPA121' requires irrigation once every 5-7 days and prefers growing under 50 $\mu mol/m^2/s$ shaded light.

Root system:

*General*.—Finely branched.

*Diameter of roots*.—1.0 mm, on average.

*Texture*.—Smooth and glabrous.

*Color*.—Grey-brown, nearest to RHS 199C.

Stem:

*General branching habit*.—Basally branching main stems; with decumbent lateral branching.

*Color of developing stems*.—Green, RHS 143C, suffused with greyed-orange, nearest to in between RHS 166A and 166B.

*Color of mature stems*.—Green, closest to RHS 143C.

*Color at internodes*.—Greyed-orange, nearest to a blend of RHS 166A and 166B.

*Texture*.—Coriaceous; trichomes present; trichomes are approximately 0.2 mm in length and colored white, RHS 155A.

*Luster*.—Matte.

*Stolons*.—Quantity — 6. Length — 5.1 cm. Diameter — 0.2 cm. Internode length — 0.3 cm. Attitude — Approximately 15-degrees from horizontal. Cross-section — Terete. Strength — Strong.

*Lateral branches*.—Quantity — 3 per stolon. Length — 3.8 cm. Diameter — 0.14 cm. Internode length — 0.3 cm. Attitude — 80-degree angle from vertical.

Foliage:

*Quantity*.—14 leaves per lateral branch.

*Arrangement*.—Opposite.

*Attachment*.—Petiolate.

*Division*.—Simple.

*Lamina*.—Shape — Elliptic. Length — 3.0 cm. Width — 1.9 cm. Apex — Acute. Base — Acute. Cross-section — Convex. Attitude — Semi-upright. Margin — Crenulate; slightly undulated. Texture and luster of the adaxial surface — Coriaceous and matte. Texture and luster of the abaxial surface — Coriaceous and matte with salient veins. Color — Juvenile foliage, adaxial surface — A blend of mid green and dark green, RHS 141A and 143A, with the entire network of veins margined with a light red coloration, RHS 38B, proximally, which transitions to a darker shade of red, RHS 52B, towards the margins and apex. This creates a prominent bright pink-on-green tessellate variegation pattern. Juvenile foliage, abaxial surface — Green, RHS 143A. Mature foliage, adaxial surface — A blend of mid green and dark green, RHS 141A and 143A, with the entire network of veins margined with a light red coloration, RHS 38B, proximally, which transitions to a darker shade of red, RHS 52B, towards the margins and apex. This creates a prominent bright pink-on-green tessellate variegation pattern. Mature foliage, abaxial surface — Green, RHS 143A. Venation — Pattern — Cross-venulate. Color — Juvenile foliage, adaxial surface — The midrib is yellow-green proximally, nearest to RHS 145A, and transitions to greyed-red, RHS 181C, towards the apex; the lateral and tertiary veins are red, RHS 51B. Juvenile foliage, abaxial surface — Yellow-green, nearest to RHS 145C. Mature foliage, adaxial surface — The midrib is a light pink coloration, RHS 51B, and transitions to yellow-green, RHS 145A, near the point of attachment; all other veins are light pink, RHS 51B. Mature foliage, abaxial surface — Yellow-green, nearest to RHS 145C.

*Petiole*.—Length — 1.9 cm. Diameter — 0.2 cm. Strength — Strong. Texture — Smooth; glabrous.

Luster — Slightly glossy. Color, adaxial surface — Yellow-green, nearest to RHS 144C and suffused with 144B. Color, abaxial surface — Yellow-green, nearest to RHS 144C.

Inflorescence: No flowering has been observed to date.

COMPARISONS WITH THE PARENT PLANT

Plants of the new cultivar 'KEJAPA121' may be distinguished from the parent plant, *Fittonia albivenis* 'Mistral' (Community Plant Variety Rights Application No 2006/1501), by the characteristics described in Table 1.

TABLE 1

Comparison between 'KEJAPA121' and 'Mistral'.

| Characteristic | 'KEJAPA121' | 'Mistral' |
|---|---|---|
| Leaf shape. | Elliptic. | Ovate. |
| Expression of variegation on the mature adaxial laminar surface. | Green, lighter than 'Mistral', with pink cross-venulate veins that are margined with a slightly lighter red color, which creates a bright pink-on-green tessellate variegation pattern. | Green, darker than 'KEJAPA121', with near-white veins that are margined with a lighter shade of red relative to 'KEJAPA121', which creates a pale pink-on-dark green tessellate variegation pattern. |

COMPARISONS WITH THE MOST SIMILAR COMMERCIAL VARIETY

Plants of the new cultivar 'KEJAPA121' may be distinguished from the most similar commercial comparator known to the inventor, *Fittonia verschaffeltii* 'Pink Star' (U.S. Plant Pat. No. 18,169), by the characteristics described in Table 2.

TABLE 2

Comparison between 'KEJAPA121' and 'Pink Star'.

| Characteristic | 'KEJAPA121' | 'Pink Star' |
|---|---|---|
| Leaf shape. | Elliptic. | Obovate to lanceolate. |
| Leaf margins. | Crenulate; slightly undulate. | Entire; highly undulate. |
| Expression of variegation on the mature adaxial laminar surface. | Green with pink cross-venulate veins that are margined with a slightly lighter red color, which creates a bright pink-on-green tessellate variegation pattern. | Green with light red cross-venulate veins that are very broadly margined with a mixture of light and dark pink, which creates a green-on-light pink flecked and blotched variegation pattern. As the foliage ages, the pink coloration bordering the venation will coalesce in the interveinal spaces. |

That which is claimed is:

1. A new and distinct variety of *Fittonia* plant named 'KEJAPA121', substantially as described and illustrated herein.

* * * * *